(12) United States Patent
Moon et al.

(10) Patent No.: US 11,351,194 B2
(45) Date of Patent: Jun. 7, 2022

(54) METHOD FOR PROLIFERATING NEURAL PROGENITOR CELLS AND COMPOSITION FOR TREATING NEUROLOGICAL DISEASES CONTAINING PROLIFERATED NEURAL PROGENITOR CELLS

(71) Applicant: COLLEGE OF MEDICINE POCHON CHA UNIVERSITY INDUSTRY-ACADEMIC COOPERATION FOUNDATION, Pocheon-si (KR)

(72) Inventors: Jisook Moon, Seoul (KR); Hyun-Seob Lee, Namyangju-si (KR); Yeon-Ho Shin, Seoul (KR)

(73) Assignee: CHA BIOTECH CO., LTD., Seoul (KR)

( * ) Notice: Subject to any disclaimer, the term of this patent is extended or adjusted under 35 U.S.C. 154(b) by 455 days.

(21) Appl. No.: 15/518,184

(22) PCT Filed: Oct. 10, 2014

(86) PCT No.: PCT/KR2014/009501
§ 371 (c)(1),
(2) Date: Apr. 10, 2017

(87) PCT Pub. No.: WO2016/056689
PCT Pub. Date: Apr. 14, 2016

(65) Prior Publication Data
US 2017/0296582 A1    Oct. 19, 2017

(51) Int. Cl.
| | |
|---|---|
| *A61K 35/12* | (2015.01) |
| *C12N 5/07* | (2010.01) |
| *C12N 5/00* | (2006.01) |
| *C12N 5/073* | (2010.01) |
| *C12N 5/079* | (2010.01) |
| *A61K 35/00* | (2006.01) |

(52) U.S. Cl.
CPC ............ *A61K 35/12* (2013.01); *C12N 5/0018* (2013.01); *C12N 5/0603* (2013.01); *C12N 5/0618* (2013.01); *A61K 35/00* (2013.01); *C12N 5/06* (2013.01); *C12N 2500/02* (2013.01); *C12N 2500/38* (2013.01); *C12N 2501/11* (2013.01); *C12N 2501/115* (2013.01); *C12N 2533/32* (2013.01); *C12N 2533/52* (2013.01)

(58) Field of Classification Search
None
See application file for complete search history.

(56) References Cited

U.S. PATENT DOCUMENTS

| | | |
|---|---|---|
| 2005/0265983 A1 | 12/2005 | Melamed et al. |
| 2013/0236436 A1 | 9/2013 | Zhang et al. |
| 2013/0236964 A1 | 9/2013 | Melamed et al. |

FOREIGN PATENT DOCUMENTS

| | | |
|---|---|---|
| AU | 2005200148 A1 | 2/2005 |
| KR | 10-2014-0130593 A | 11/2014 |
| WO | WO 2007/142449 A1 | 12/2007 |

OTHER PUBLICATIONS

Zhao et al., FEBS J. (2008) 275:1824-1834.*
Brewer et al., J. Neurosci. Res. (1993) 35:567-476.*
Brewer et al., Brain Res. 1989, 494(1)65-74 (Year: 1989).*
Dhara et al. Differentiation 2008, 76:45 (Year: 2008).*
Wang et al., J. Neurosci., 2005, 25(19):4706-4718 (Year: 2005).*
International Search Report dated Jun. 29, 2015, in PCT/KR2014/009501 filed Oct. 10, 2014.
"Neuronal Stem Cell Supplement", Brochure, PAA the Cell Culture Company, (2011), 33 pages.
Santilli et al., "Mild Hypoxia Enhances Proliferation and Multipotency of Human Neural Stem Cells", PLoS One, vol. 5, No. 1, Paper No. e8575 , (2010), 12 pages.
Kosaka, et al., "FGF-4 regulates neural progenitor cell proliferation and neuronal differentiation", The FASEB Journal, vol. 20, No. 9, pp. 1484-1485, (2006), 9 pages.
Extended European Search Report dated Mar. 21, 2018 in European Patent Application No. 14903548.7, 8 pages.
Wachs, Frank-Peter, et al., "High Efficacy of Clonal Growth and Expansion of Adult Neural Stem Cells", Laboratory Investigation, XP055057829. vol. 83 No. 7, Jul. 2003, pp. 949-962.
Deng, Sihao, et al., "Vitamin E isomer δ-tocopherol Enhances the Efficiency of Neural Stem Cell Differentiation via L-type Calcium Channel", Neuroscience Letters, XP029117324, vol. 585, Nov. 20, 2014, pp. 166-170.
Office Action dated Feb. 18, 2019 in the corresponding European Patent Application No. 14 903 548.7 7 pages.
Zhanqiu Yang, et al., "Culture Conditions and Types of Growth Media for Mammalian Cells", pp. 1-18, Intech, 2012.
Meenakshi Arora, Ph.D., Cell Culture Media: A Review, pp. 1-27, Labome, Oct. 30, 2013.
Claire M. Kelly, et al., "The Effects of Various Concentrations of FGF-2 on the Proliferation and Neuronal Yield of Murine Embryonic Neural Precursor Cells In Vitro", pp. 215-223, vol. 12, Cell Transplantation, 2003.

(Continued)

*Primary Examiner* — James D Schultz
(74) *Attorney, Agent, or Firm* — Oblon, McClelland, Maier & Neustadt, L.L.P.

(57) ABSTRACT

The present invention provides a method for proliferating neural progenitor cells and a composition for treating neurological diseases, the composition including a proliferated neural progenitor cell. When a fetal neural progenitor cell is cultured under a hypoxia condition and/or in a medium containing tocoperol, tocoperol acetate, or a mixture thereof, the improved cell proliferation rates of the fetal neural progenitor cell are confirmed. In addition, considering an effect of the neural progenitor cell on preventing differentiation thereof into neurons at the time of proliferation, the present disclosure may contribute to mass production of neural stem cells, and accordingly, the proliferated neural progenitor cell is expected to be utilized in the treatment of a neurological disease.

12 Claims, 12 Drawing Sheets

(56) References Cited

OTHER PUBLICATIONS

Panagiota A. Sotiropoulou, et al., "Characterization of the Optimal Culture Conditions for Clinical Scale Production of Human Mesenchymal Stem Cells", pp. 462-471, 24; Stem Cells Technology Development, 2006.

Gioele La Manno, et al., "Molecular Diversity of Midbrain Development in Mouse, Human, and Stem Cells", pp. 566-580, 167(2), Cell, Oct. 6, 2016.

Jan H. Lui, et al., "Development and Evolution of the Human Neocortex", pp. 18-36, 146 (1), Cell, Jul. 8, 2011.

* cited by examiner

METHOD FOR PROLIFERATING NEURAL PROGENITOR CELLS AND COMPOSITION FOR TREATING NEUROLOGICAL DISEASES CONTAINING PROLIFERATED NEURAL PROGENITOR CELLS

TECHNICAL FIELD

The present invention relates to a method of proliferating neural progenitor cells and a composition containing a proliferated neural progenitor cells for treating a neurological disease.

BACKGROUND ART

Neurological diseases are a wide range of diseases in which nerve cells in either a central nervous system or a peripheral nervous system die or malfunction. In particular, degenerative neurological diseases are known to be caused by, with age, apoptosis of neurons, problems in formation of synapses among neurons, or malfunctions of synapses.

Neural stem cells are cells capable of being continuously proliferating in an undifferentiated state, and at the same time, of being differentiated into diverse types of neurons. Such neural stem cells exist in various anatomical regions and form the nervous system in the fetal period and it has been known that neural stem cells are not regenerated once damaged. Neural stem cells also exist in the central nervous system of adult mammals, and are proliferating and differentiated throughout the life to produce new neurons. Neural stem cells can be cultured in vitro for the long term, and can be integrated into the nervous system of a host by engraftment, migration, and differentiation during in vivo transplantation. Accordingly, there is a growing interest in the possibility of nerve regenerative therapy using neural stem cells in neurological diseases.

In consideration of the clinical application of neural stem cells, there is a need to establish a technique for inducing differentiation of the neural stem cells into appropriate neurons while the neural stem cells are safely cultured and proliferate in a sufficient amount by identifying the mechanisms of proliferation, growth, and differentiation of the neural stem cells. Since neural stem cells have the ability to differentiate into a desired cell type, the neural stem cells may be useful for cell therapy by improving the proliferation capacity of the neural stem cells.

DETAILED DESCRIPTION OF THE INVENTION

Technical Problem

An aspect of the present disclosure provides a method for proliferation of stem cells, the method including culturing a stem cell in a medium containing tocopherol, tocopherol acetate, or a mixture thereof.

Another aspect of the present disclosure provides a composition for treating a neurological disease. The composition includes the neural progenitor cells that are produced according to the method above.

Another aspect of the present disclosure provides a culture composition containing tocopherol, tocopherol acetate, or a mixture of them for proliferating neural progenitor cells in an undifferentiated state.

Technical Solution

An aspect of the present disclosure provides a method for proliferation of stem cells, the method including culturing stem cells in a medium containing tocopherol, tocopherol acetate, or a mixture thereof.

The stem cell may be cultured under a hypoxia condition. The hypoxia condition may include, for example, atmospheric oxygen at a concentration in a range of about 0.1% to about 10%, about 1% to about 10%, about 1% to about 8%, about 1% to about 5%, about 2% to about 5%, or about 2% to about 3%.

The stem cell proliferated according to the method above may be used to treat or prevent various diseases. The diseases may include, for example, blood vessel or cardiovascular disease, arteriosclerosis, diabetes, aplastic anemia, ischemia, myelodysplasia, myocardial infraction, fainting, multiple sclerosis, seizure, stroke, hypotension, cardiac arrest, ischemia, inflammation, age-related cognitive loss, radiation hazard, cerebral apoplexy, neurodegenerative disease, Alzhimer's disease, Parkinson's disease, Parkinson's disease dementia, Huntington's disease, Leigh's disease, AIDS dementia, memory loss, amyotrophic lateral sclerosis (ALS), multiple system atrophy, ischaemic heart disease, brain or spinal cord injury, neurological disease caused by spinal cord injury, cardiopulmonary bypass, glaucoma, retinal ischemia, lysosomal storage disease, such as Niemarm-Pick disease, Fabry's disease, Gaucher's disease, Hunters disease, Hurlers syndrome, mucopolysaccharidosis, glycogenosis such as glycogen storage disease, congenital metabolic disorder, adrenoleukodystrophy, cystic fibrosis, hypothyroidism, sickle-cell anaemia, Pearson's syndrome, Pompe's disease, phenylketonuria (PKU), porphyrias, maple-syrup urine disease, homocystinuria, chronic Granulomatous disease, tyrosinemia, Tay-Sachs disease, cancer, tumor, and other pathological or oncological conditions, but examples of the diseases are not limited thereto.

The stem cell may be a neural progenitor cell. The term "a neural progenitor cell (or a neuronal precursor cell)" as used herein refers to a cell that can be differentiated into various types of neurons. The neural progenitor cell may be used interchangeably with a neural stem cell. In addition, the neural progenitor cell may refer to a cell derived from a neural stem cell. The neural progenitor cell may be, for example, derived from a mammalian fetus or adult. The neural progenitor cell may be, for example, derived from a brain tissue of the mammalian fetus. The neural progenitor cell may be, for example, derived from a ventral midbrain tissue of the mammalian fetus. In addition, the neural progenitor cell may be obtained by differentiation of the cells derived from human embryonic stem cells (hESCs), induced pluripotent stem cells (iPSCs), human adult stem cells, human hematopoietic stem cells, human mesenchymal stem cells (hMSCs), or immortailized cell lines derived from human fetal neural tissue according to a known method disclosed in Yiping Yana, et al., Directed Differentiation of Dopaminergic Neuronal Subtypes from Human Embryonic Stem Cells, Stem Cells. 2005; 23(6): 781-790; Yan Li, et al., Neural differentiation from pluripotent stem cells: The role of natural and synthetic extracellular matrix, World J Stem Cells 2014 January 26; 6(1): 11-23; Lorena Arranz, el al., Neuropathy of haematopoietic stem cell niche is essential for myeloproliferative neoplasms, Nature. 2014 Aug. 7; 512(7512):78-81; and Liang Xu, el al., The iPS Technique Provides Hope for Parkinson's Disease Treatment, Stem Cell Rev and Rep (2010) 6:398-404.

The stem cells may, for example, proliferate in an undifferentiated state. The term "proliferation" as used herein refers to an increase in the number of cells. The proliferation in an undifferentiated state means proliferation of a cell into cells having the same properties as the original cell without being differentiated into specific cells.

Tocopherol or tocopherol acetate in the medium may be, for example, alpha-tocopherol or alpha-tocopherol acetate. The media may contain tocopherol, tocopherol acetate, or a mixture at a concentration in a range of, for example, about 0.01 µg/ml to about 50 µg/ml, about 0.01 µg/ml to about 40 µg/ml, about 0.01 µg/ml to about 30 µg/ml, about 0.01 µg/ml to about 20 µg/ml, about 0.01 µg/ml to about 10 µg/ml, or about 1 µg/ml to about 10 µg/ml. The mixture of tocopherol and tocopherol acetate may be added in the medium at a ratio in a range of about 1:10 to about 10:1, about 1:5 to about 5:1, about 1:4 to about 4:1, about 1:3 to about 3:1, or about 1:2 to about 2:1, or at a ratio of about 1:1.

The medium may, for example, be prepared by containing tocopherol and/or tocopherol acetate in a cell culture medium typically used in the art. The cell culture medium may be, for example, Dulbecco's Modified Eagle's Medium (DMEM, manufactured by GIBCO, USA), Minimal Essential Medium (MEM, manufactured by GIBCO, USA), Basal Medium Eagle (BME, manufactured by GIBCO, USA), RPMI 1640 (manufactured by GIBCO, USA), DMEM/Nutrient Mixture F-10 (DMEM/F10, manufactured by GIBCO, USA), DMEM/Nutrient Mixture F-12 (DMEM/F12, manufactured by GIBCO, USA), α-Minimal Essential Medium (α-MEM, manufactured by GIBCO, USA), Glasgow's Minimal Essential Medium (G-MEM, manufactured by GIBCO, USA), or Isocove's Modified Dulbecco's Medium (IMDM, manufactured by GIBCO, USA). The medium may further include an antibiotic, a B27 supplement, and/or a growth factor. The antibiotic may be, for example, penicillin, streptomycin, gentamicin, or Primocin™. The growth factor may be, for example, basic fibroblast growth factor (bFGF), epidermal growth factor (EGF), and/or fibroblast growth factor 4 (FGF4). Here, bFGF, EGF, or FGF4 may be included in the medium at a concentration in a range of, for example, about 2 ng/ml to about 100 ng/ml, about 4 ng/ml to about 80 ng/ml, about 5 ng/ml to about 50 ng/ml, or about 10 ng/ml to about 30 ng/ml.

The method may be a method for proliferating neural progenitor cells, the method including culturing a neural progenitor cell in a medium containing tocopherol, tocopherol acetate, or a mixture thereof and under a hypoxia condition. The hypoxia condition may include, for example, atmospheric oxygen at a concentration in a range of about 0.1% to about 10%, about 1% to about 10%, about 1% to about 8%, about 1% to about 5%, about 2% to about 4%, or about 2% to about 3%. The neural progenitor cells may proliferate in an undifferentiated state. Tocopherol or tocopherol acetate contained in the medium may be, for example, alpha-tocopherol or alpha-tocopherol acetate. A concentration of tocopherol, tocopherol acetate, or a mixture thereof contained in the medium and a mixing ratio of tocopherol and tocopherol acetate are the same as described above. The medium may be prepared by containing tocopherol and/or tocopherol acetate in a cell culture medium typically used in the art. The cell culture medium may be the same as described above. The medium may further include, for example, an antibiotic, a B27 supplement, and/or a growth factor. The antibiotic and the growth factor are respectively the same as described above.

Another aspect of the present disclosure provides a composition for treating a neurological disease, the composition including neural progenitor cells that are produced in a medium containing tocopherol, tocopherol acetate, or a mixture thereof.

The neural progenitor cells may be, for example, cultured under a hypoxia condition. The hypoxia condition may include, for example, atmospheric oxygen at a concentration in a range of about 0.1% to about 10%, about 1% to about 10%, about 1% to about 8%, about 1% to about 5%, about 2% to about 4%, or about 2% to about 3%. Tocopherol or tocopherol acetate in the medium may be, for example, alpha-tocopherol or alpha-tocopherol acetate. A concentration of tocopherol, tocopherol acetate, or a mixture thereof in the medium may be in a range of, for example, about 0.01 µg/ml to about 50 µg/ml, about 0.01 µg/ml to about 40 µg/ml, about 0.01 µg/ml to about 30 µg/ml, about 0.01 µg/ml to about 20 µg/ml, about 0.01 µg/ml to about 10 µg/ml, or about 1 µg/ml to about 10 µg/ml. Tocopherol and tocopherol acetate in the medium may be added as mixture at a ratio in a range of about 1:10 to about 10:1, about 1:5 to about 5:1, about 1:4 to about 4:1, about 1:3 to about 3:1, or about 1:2 to about 2:1, or at a ratio of about 1:1. The medium may be prepared by addition of tocopherol and/or tocopherol acetate in a cell culture medium typically used in the art. The cell culture medium is the same as described above. The medium may further include, for example, an antibiotic, a B27 supplement, and/or a growth factor. The antibiotic and the growth factor are respectively the same as described above.

The neurological disease may be, for example, a disease selected from the group consisting of Parkinson's disease, Alzheimer's disease, Huntington's disease, amyotrophic lateral sclerosis, multiple system atrophy, Parkinson's disease dementia, stroke, ischemia, and neurological disease caused by spinal cord injury.

Another aspect of the present disclosure provides a culture composition containing tocopherol, tocopherol acetate, or a mixture thereof for proliferating a neural progenitor cell in an undifferentiated state.

Tocopherol or tocopherol acetate contained in the culture composition may be alpha-tocopherol or alpha-tocopherol acetate. Tocopherol, tocopherol acetate, or a mixture thereof in the culture composition may be at a concentration in a range of, for example, about 0.01 µg/ml to about 50 µg/ml, about 0.01 µg/ml to about 40 µg/ml, about 0.01 µg/ml to about 30 µg/ml, about 0.01 µg/ml to about 20 Jig/ml, about 0.01 µg/ml to about 10 µg/ml, or about 1 µg/ml to about 10 µg/ml. Tocopherol and tocopherol acetate in the culture composition may be mixed at a ratio in a range of about 1:10 to about 10:1, about 1:5 to about 5:1, about 1:4 to about 4:1, about 1:3 to about 3:1, or about 1:2 to about 2:1, or at a ratio of about 1:1. The culture composition may be prepared by containing tocopherol and/or tocopherol acetate in a cell culture medium typically used in the art. The cell culture medium may be the same as described above. The cell culture medium may further include, for example an antibiotic, a B27 supplement, and/or a growth factor. The antibiotic and the growth factor are respectively the same as described above.

Advantageous Effects of the Invention

A method of proliferating a stem cell according to an aspect of the present disclosure can contribute to the mass production of the stem cells. Accordingly, the proliferated stem cells are expected to be useful in the treatment of various diseases.

DESCRIPTION OF THE DRAWINGS

FIG. 2 shows results of microscopic examination (see FIG. 2A) and cytometry (see FIG. 2B), on fetal neural progenitor cells that were cultured in each medium for 7 days.

BEST MODE

Hereinafter, the present invention will be described more fully with reference to the following examples. However, these examples are for illustrative purposes only, and thus, should not be construed as being limited to the examples set forth herein.

Example 1. Measurement of Cell Viability by 3-(4,5-dimethyltriazole-2-yl)-2,5-diphenyl Tetrazolium Bromide (MTT) Assay Human neural progenitor cells were isolated from 14 week-old human fetuses. Before obtaining the fetus samples, informed consents that had been sufficiently described to parents in advance were received. In addition, the sample collection and use thereof for research were approved by the Institutional Review Board of the CHA Hospital. Ventral midbrain tissues in the brain of a 14-week-old human fetus were isolated according to the method disclosed in Storch et al. 2001; and Milosevic et al. 2006, 2007, and then, dissociated into a single cell suspension by treating the ventral midbrain tissues in a solution containing 0.1 mg/ml of papain and 100 µg/ml of DNase at a temperature of 37° C. for about 30 minutes. The single cell suspension was washed with phosphate buffered saline (PBS), and then, incubated in 50 µg/ml of antipain at a temperature of 37° C. for 30 minutes. The resulting neural progenitor cells were plated, in a monolayer, at a density of 30,000 cells/cm$^2$, onto a culture dish that was pre-coated with 15 µg/ml of poly-L-omithine and 4 µg/ml of fibronectin, and then, cultured. The cultured fetus neural progenitor cells were seeded on a 96-well plate at a density of 1×10$^4$ cells/well, cultured for 7 days, and treated with an MTT reagent. Then, by measuring optical density thereof (at a wavelength of 570 nm), the cell viability was analyzed.

Figure 1:
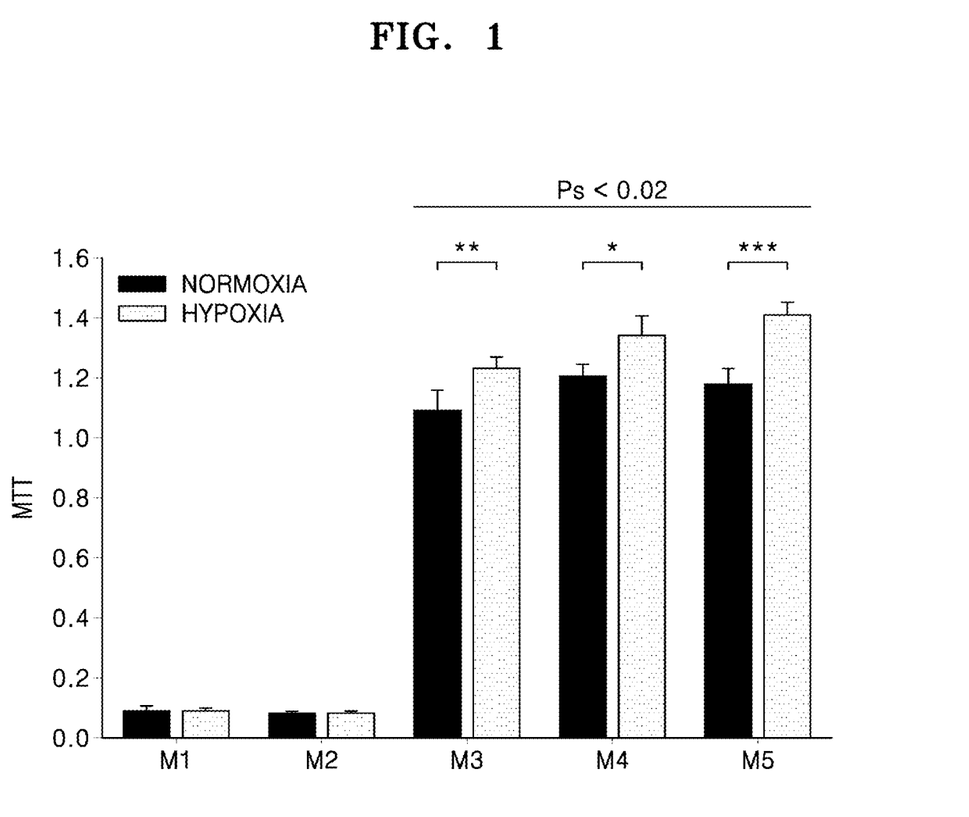
FIG. 1 shows results obtained by cell viability through an MTT assay after fetal neural progenitor cells were cultured in each medium for 7 days.

FIG. 1 shows results obtained by cell viability through an MTT assay after fetal neural progenitor cells were cultured in each medium for 7 days. 20 ng/ml of each of bFGF and EGF (available from Peprotech, R&D system) and 10 ml of a B27 supplement (available from GIBCO) were added to 500 ml of a mixed medium of DMEM/F12 (1:1) containing 0.5 ml of Primocin, which is an antibiotic formulation, and then, the fetal neural progenitor cells were cultured under a condition in which 1 µg/ml of DL-alpha-tocopherol acetate (M3), 1 µg/ml of (t)-alpha-tocopherol (M4), or a combination thereof (M5) was added. The resulting fetal neural progenitor cells were compared with those cultured under a general culture condition. Regarding the general culture condition, 20 ng/ml of each of bFGF and EGF and an α-supplement (2.5 mg insulin, 25 mg transferrin, 0.03 µM sodium selenite, 36.5 mg L-glutamine, and 0.75 g L-glucose) were added to 500 ml of a mixed medium of DMEM/F12 (1:1) containing 0.5 ml of Primocin, which is an antibiotic formulation, and then, the fetal neural progenitor cells were cultured therein (M1), or under a condition in which the B27 supplement was further added (M2).

As a result, in comparison with the fetal neural progenitor cells cultured under the general culture condition, the medium containing alpha-tocopherol and/or DL-alpha-tocopherol acetate showed higher cell viability that is statistically significant (Ps<0.02). In addition, in comparison with the fetal neural progenitor cells cultured under a normoxia condition, the medium under a hypoxia condition containing atmospheric oxygen in a range of about 0.1% to about 10% showed higher cell viability that is statistically significant (M3: P<0.009, M4: P<0.01, M5: P<0.001).

Therefore, it was confirmed that the cell viability of the fetus neural progenitor cells increased upon the treatment of DL-alpha-tocopherol acetate and/or alpha-tocopherol, and more particularly, such a synergistic effect was shown under a hypoxia condition.

Example 2. Cytometry

The fetal neural progenitor cells were seeded on a 6-well plate at a density of 2×10$^5$ cells/well, cultured for 7 days, and then subjected to cytometry.

Figure 2A:
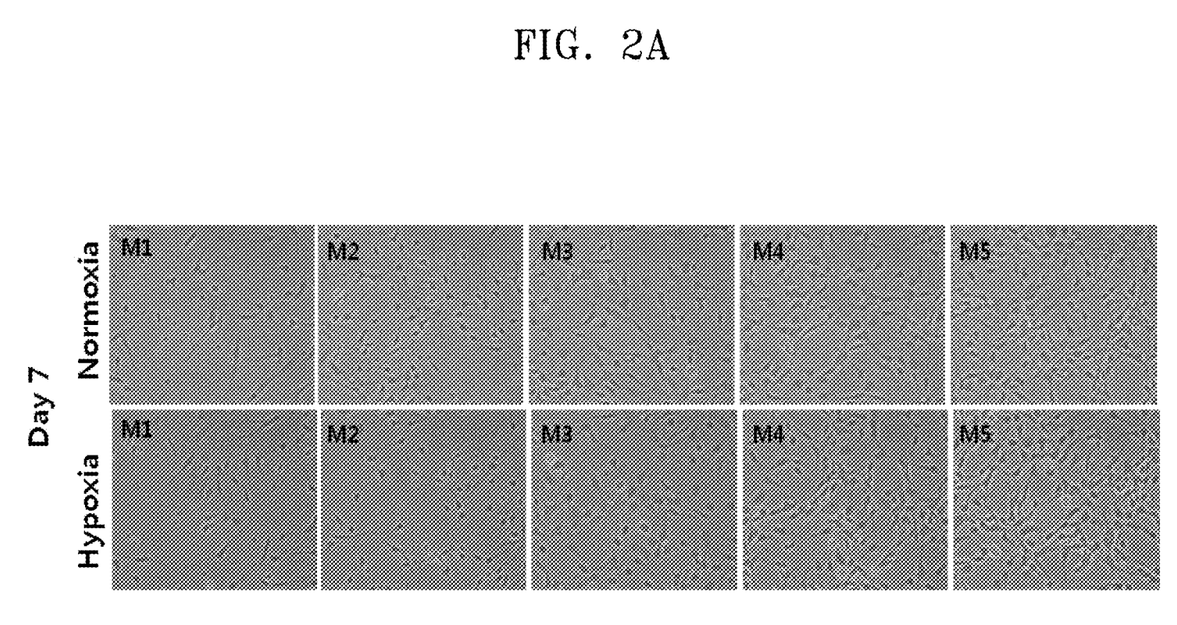
Figure 2B:
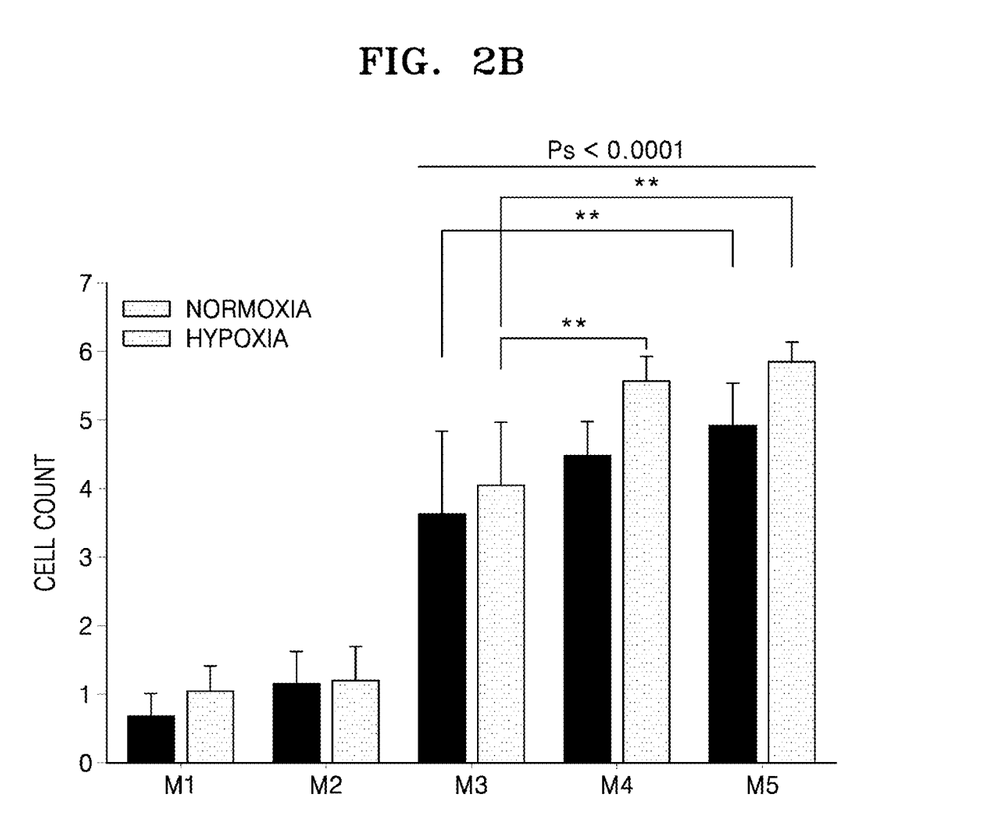

FIG. 2 shows microscopic examination (see FIG. 2A) and cytometry (see FIG. 2B), on the fetal neural progenitor cells that were cultured in each medium for 7 days. Here, each culture condition from M1 to M5 was the same as described in Example 1. Compared to the fetal neural progenitor cells cultured under a general condition, the significantly increased number of fetal neural progenitor cells was detected when fetal neural progenitor cells were cultured in a medium containing 1 µg/ml of alpha-tocopherol and/or 1 µg/ml of DL-alpha-tocopherol acetate (Ps<0.0001). Under hypoxia, in comparison with a single treatment either DL-alpha-tocopherol acetate or alpha-tocopherol, combinatorial treatment with both DL-alpha-tocopherol acetate and alpha-tocopherol increased the number of fetal neural progenitor cells of significance (M3 vs. M4: P<0.003, M3 vs. M5: P<0.0006). Under a normoxia condition, in comparison with addition of DL-alpha-tocopherol acetate only, treatment of both DL-alpha-tocopherol acetate and alpha-tocopherol showed a statistically significant increase in the number of fetal neural progenitor cells (M3 vs. M5: P<0.009).

Consequently, the greatest number of fetal neural progenitor cells was confirmed in the experimental groups treated with both DL-alpha-tocopherol acetate and alpha-tocopherol.

Example 3: Immunocytochemistry Analysis 1

The fetal neural progenitor cells were seeded on a 24-well plate at a density of 1×10$^5$ cells/well, cultured for 7 days, and then, subjected to immunocytochemistry analysis using Ki67, Nestin, and DAPI markers.

FIGS. 3A to 3D each shows the comparison of expression rates of Ki67, Ki67+Nestin upon Dapi markers in a medium after the fetal neural progenitor cells were cultured in each medium for 7 days and then subjected to immunostaining.

Figure 3A:
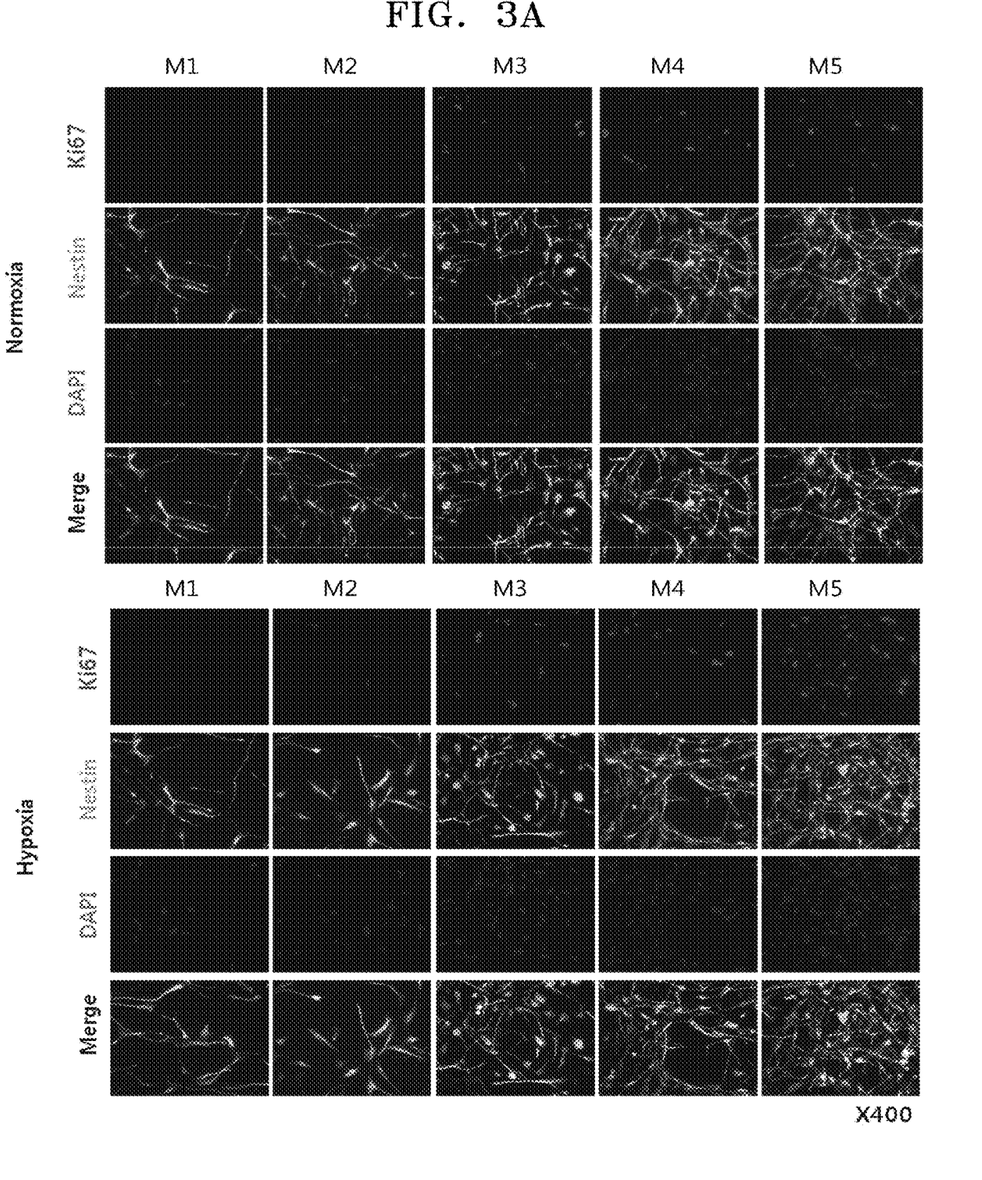
FIGS. 3A to 3D each shows comparison of expression rates of Ki67, Ki67+Nestin upon Dapi markers in a medium after the fetal neural progenitor cells were cultured in each medium for 7 days and then subjected to immunostaining.
Figure 3B:
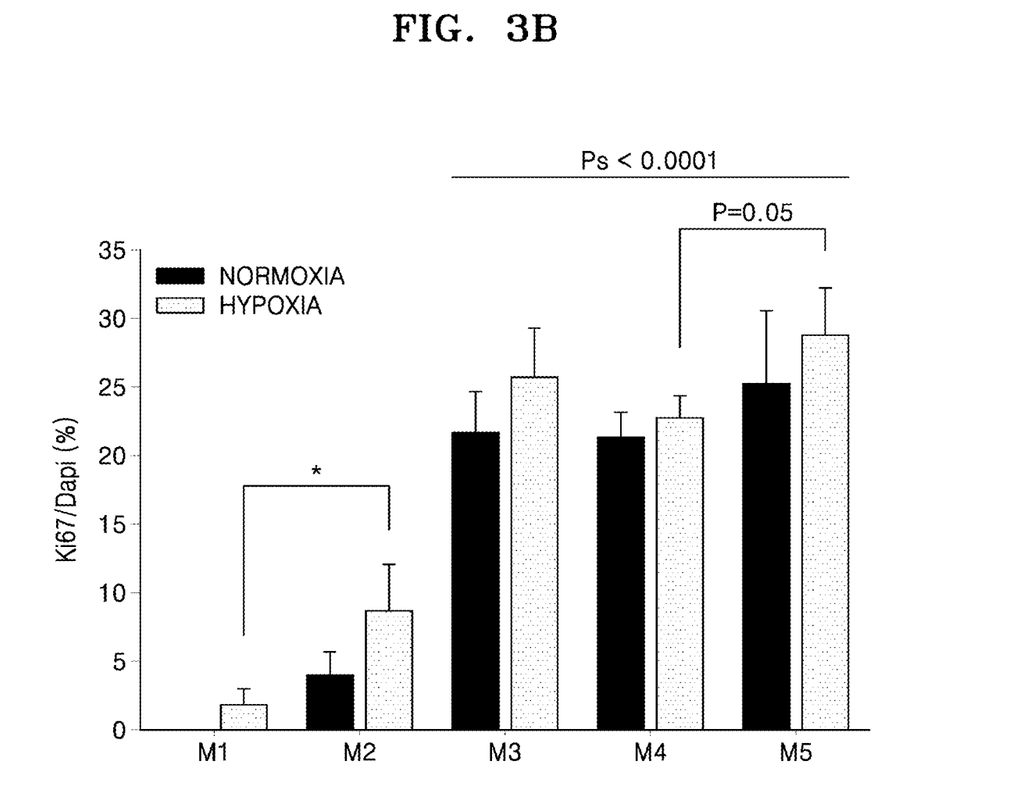

In FIG. 3B, in comparison with the fetal neural progenitor cells that were cultured in M1 and M2 which represent a general culture condition, the fetal neural progenitor cells that were in M3 with DL-alpha-tocopherol acetate only, M4 with alpha-tocopherol only, or M5 with both DL-alpha-tocopherol acetate and alpha-tocopherol displayed increased expression of Ki67 of significance (Ps<0.0001). Under a hypoxia condition, in comparison with addition of alpha-tocopherol alone, supplement of both DL-alpha-tocopherol acetate and alpha-tocopherol marginally induced more expression of Ki67 (M4 vs. M5: P=0.05). Among the general culture conditions, addition of B27 supplement (M2) showed increased expression of Ki67 in a statistically significant manner, as compared to absence of the B27 supplement (M1) (Ps<0.03).

Figure 3C:
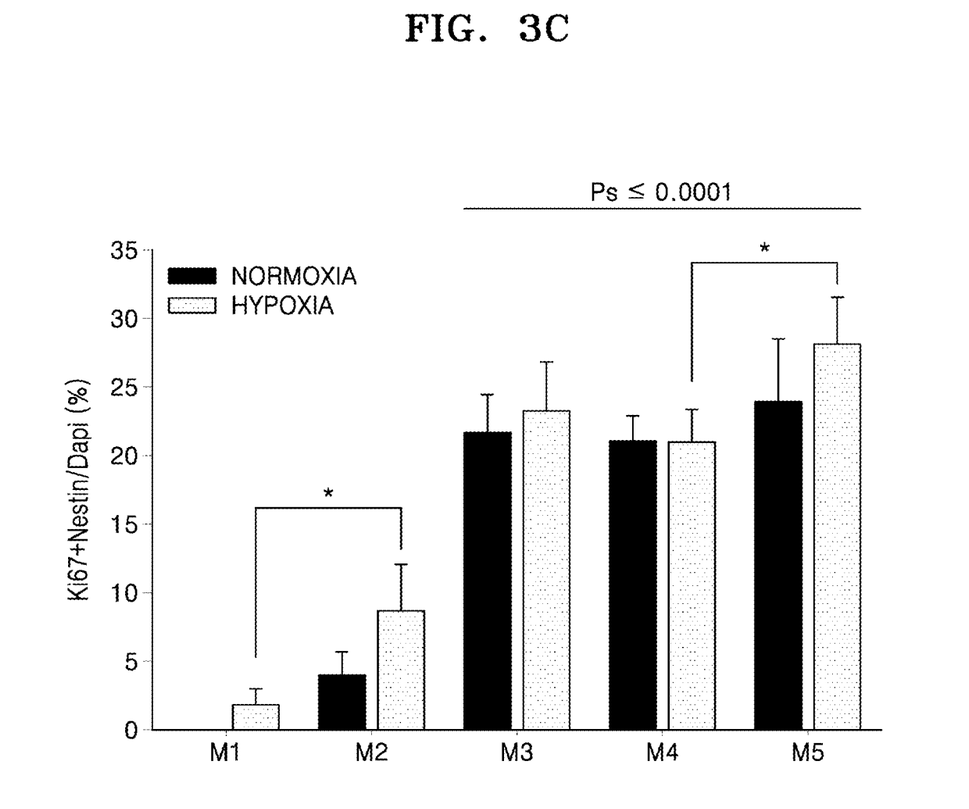
Figure 3D:
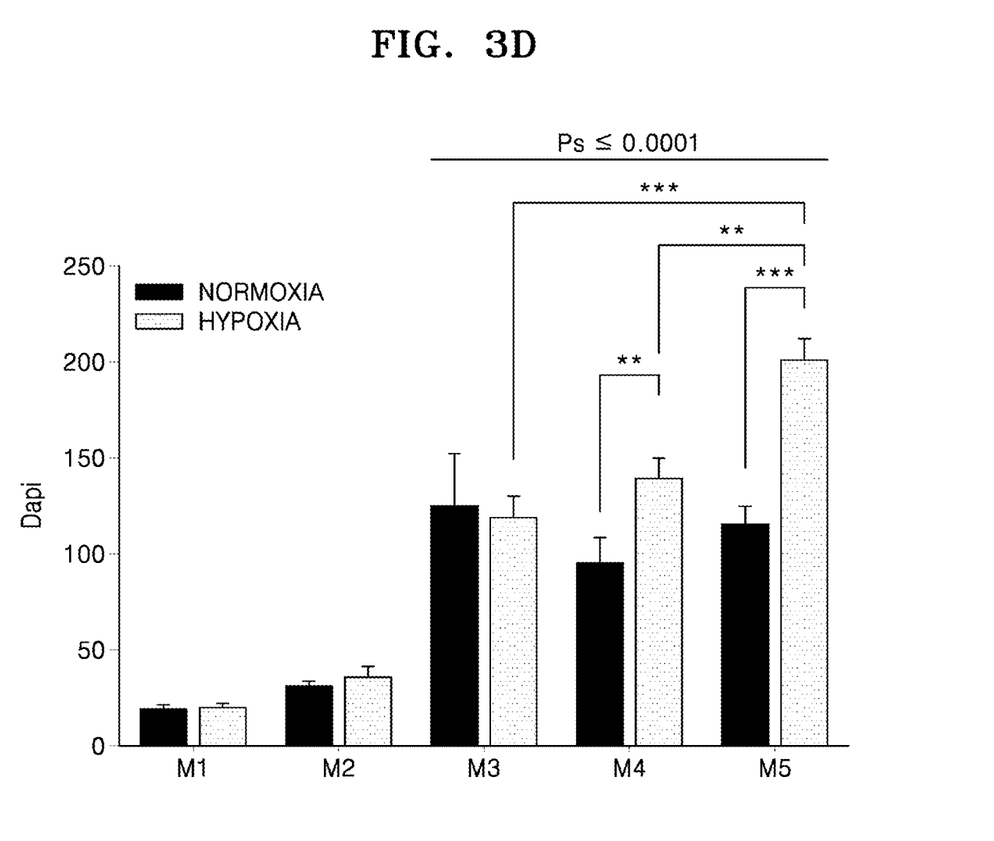

In FIG. 3C, in comparison with the fetal neural progenitor cells cultured under the general culture condition, the neural progenitor cells cultured with DL-alpha-tocopherol acetate, alpha-tocopherol, or both DL-alpha-tocopherol acetate and alpha-tocopherol showed higher frequency of expression of both Ki67 and Nestin together in a statistically significant manner (Ps≤0.0001). Among the hypoxia conditions, in comparison with addition of alpha-tocopherol only, supplement of both DL-alpha-tocopherol acetate and alpha-tocopherol led to higher frequency of expression of both Ki67 and Nestin both of significance (M4 vs. M5, P<0.02). In FIG. 3D, in comparison with the fetal neural progenitor cells cultured under normoxia, the fetal neural progenitor cells cultured under hypoxia showed increased expression of Dapi ($F_{4, 48}$=57.91, P<0.0001). In addition, in comparison with the fetal neural progenitor cells that were cultured under normoxia, the fetal neural progenitor cells cultured with DL-alpha-tocopherol acetate, alpha-tocopherol, or both DL-alpha-tocopherol acetate and alpha-tocopherol showed statistically significant increase in the expression of Dapi (Ps≤0.0001). Among hypoxia conditions, in comparison with the fetal neural progenitor cells cultured with either DL-alpha-tocopherol acetate or alpha-tocopherol alone, the fetal neural progenitor cells cultured with both DL-alpha-tocopherol acetate and alpha-tocopherol showed statistically significant increase in the expression of Dapi (M3 vs. M5, P<0.0001, M4 vs. M5, P<0.0002). Under the conditions in which only alpha-tocopherol was added and both DL-alpha-tocopherol acetate and alpha-tocopherol were added, the fetal neural progenitor cells showed statistically significant increase in the expression of Dapi under such hypoxia conditions as compared with those cultured under a normoxia condition (in comparison with the normoxia condition, M4 and M5 of the hypoxia conditions had P<0.006 and P<0.0001, respectively).

Therefore, it was confirmed that the experimental groups treated with both DL-alpha-tocopherol acetate and alpha-tocopherol showed higher expression of Dapi, high percentage of cells showing positive Ki67, a proliferation marker, or high percentage of cells showing positive Ki67 and positive Nestin, a neural progenitor cell marker (see FIGS. 3B to 3D).

Example 4: Immunocytochemistry Analysis 2

The neural progenitor cells were seeded on a 24-well plate at a density of 1×10⁵ cells/well, cultured for 7 days, and then, subjected to immunocytochemistry analysis using GFAP, Tuj1, and DAPI markers.

FIGS. 4A to 4E each shows comparison of expression rates of GFAP, Tuj1, GFAP+Tuj1, and Dapi markers in a medium after the fetal neural progenitor cells were cultured in each medium for 7 days and then subjected to immunostaining.

Figure 4A:
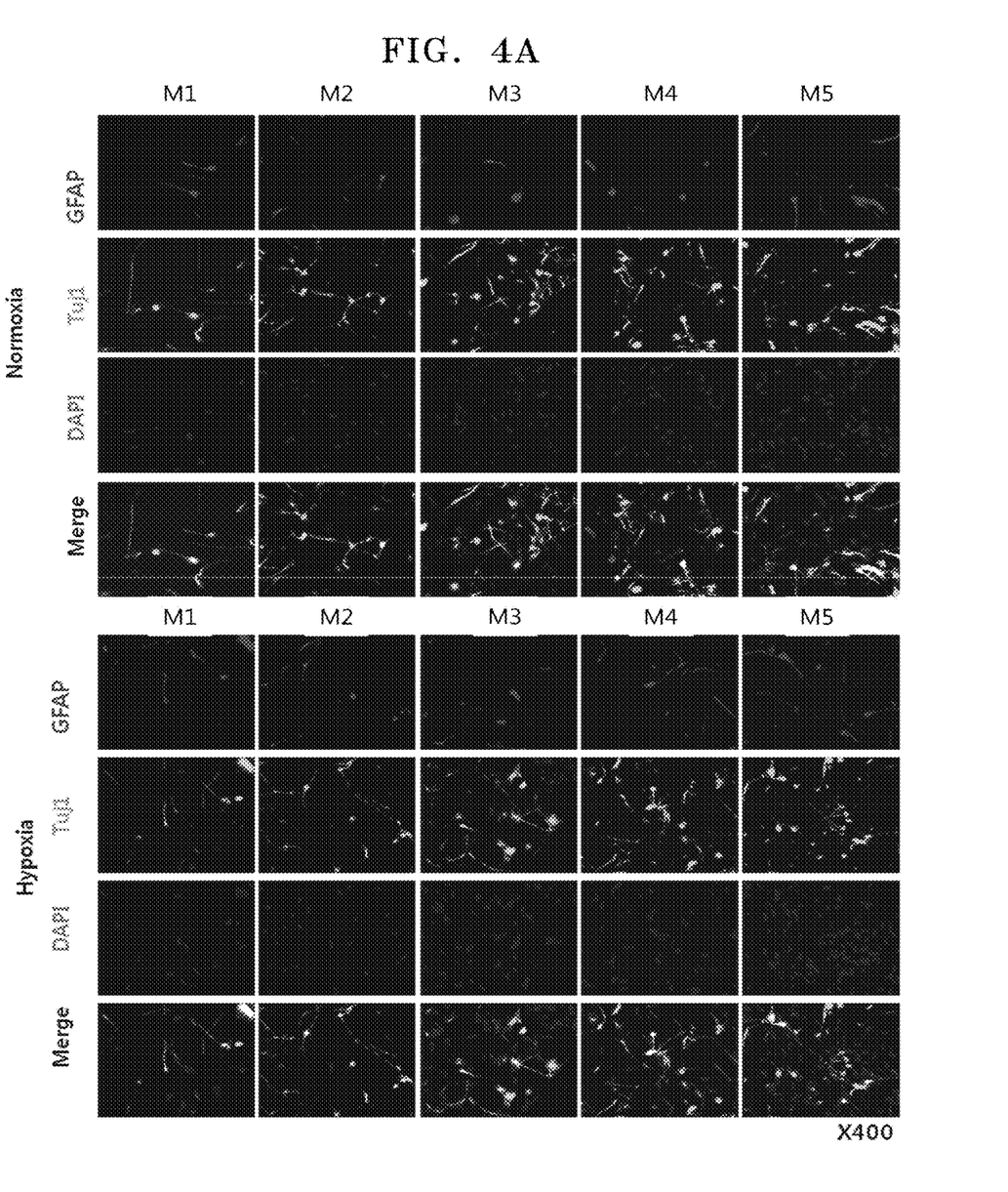
FIGS. 4A to 4E each shows results of comparing expression rates of GFAP, Tuj1, GFAP+Tuj1 upon Dapi markers in a medium after the fetus neural progenitor cells were cultured in each medium for 7 days and then subjected to immunostaining.
Figure 4B:
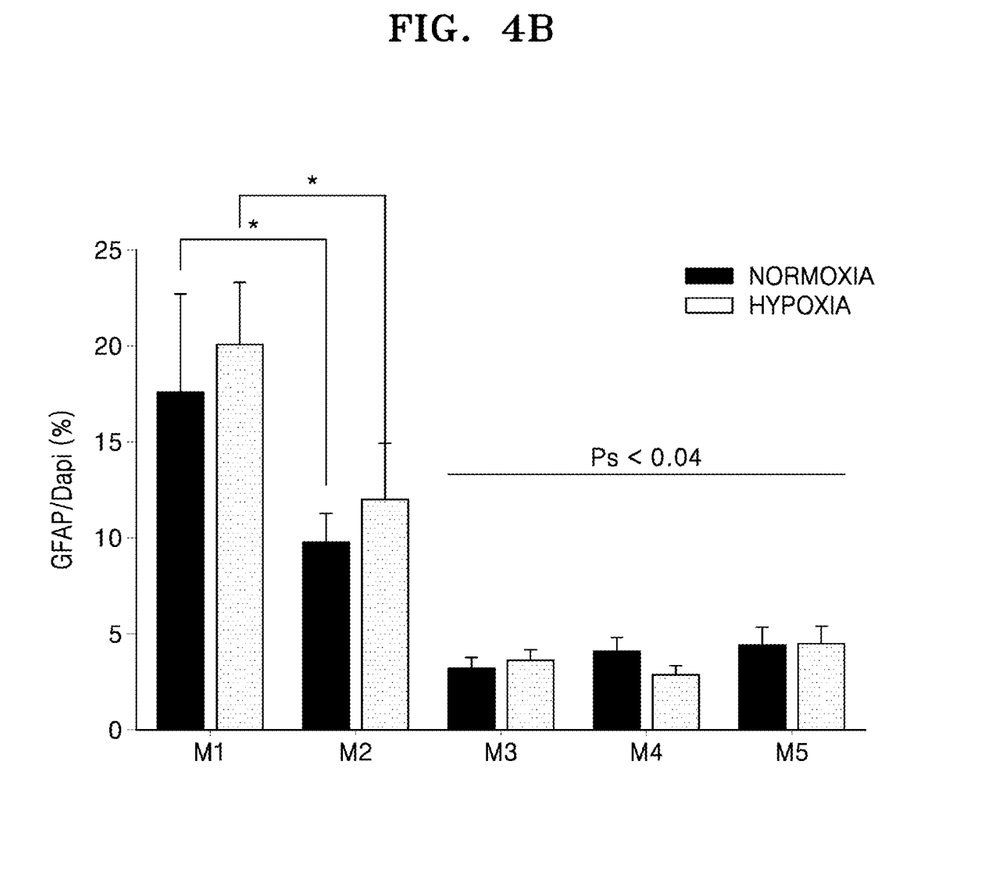

In FIG. 4B, in comparison with the fetal neural progenitor cells cultured in M1 and M2, which each represent a general culture condition, the fetal neural progenitor cells that were in M3 including DL-alpha-tocopherol acetate only, M4 including alpha-tocopherol only, or M5 including both DL-alpha-tocopherol acetate and alpha-tocopherol showed reduced expression of GFAP in a statistically significant manner (Ps<0.04). In addition, among the general culture conditions, addition of the B27 supplement (M2) reduced expression of GFAP of significance compared to absence of the B27 supplement (M1) (hypoxia condition: P<0.006, general normoxia condition: P<0.007).

Figure 4C:
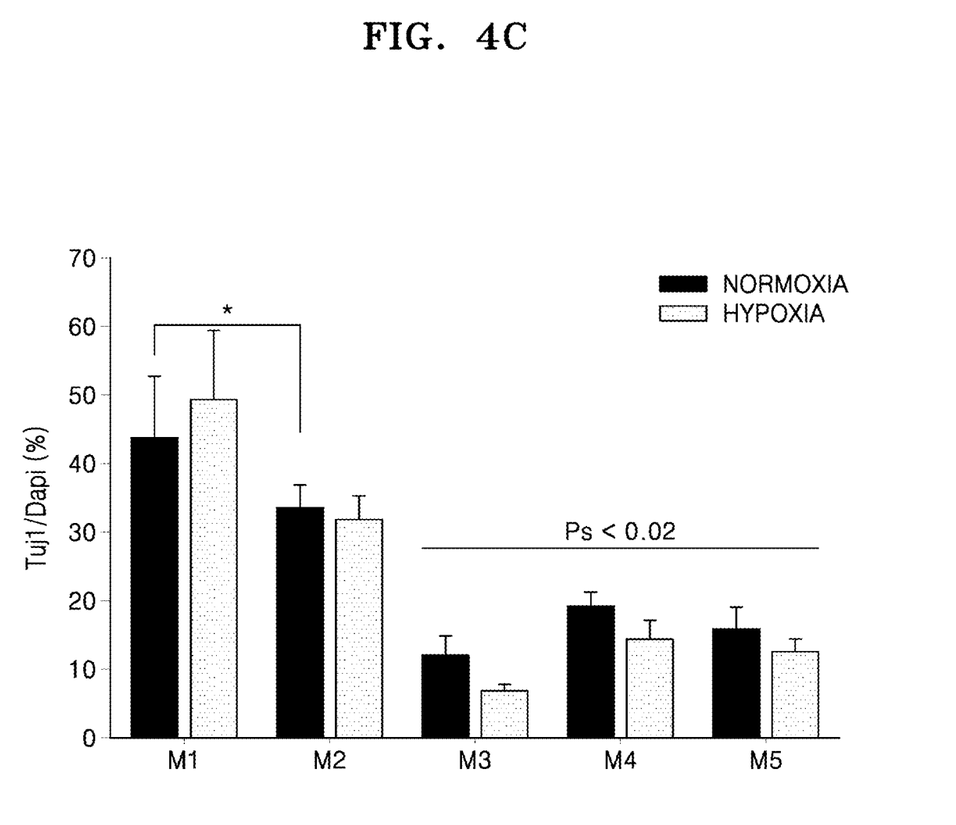

In FIG. 4C, in comparison with the fetal neural progenitor cells cultured in M1 and M2, which each represent a general culture condition, the fetal neural progenitor cells that were in M3 including DL-alpha-tocopherol acetate only, M4 including alpha-tocopherol only, or M5 including both DL-alpha-tocopherol acetate and alpha-tocopherol showed reduced expression of Tuj1 in a statistically significant manner (Ps<0.02). In addition, among the general culture conditions, addition of the B27 supplement (M2) significantly reduced expression of Tuj1, as compared to a case without the B27 supplement (M1) (hypoxia condition: P<0.008).

Figure 4D:
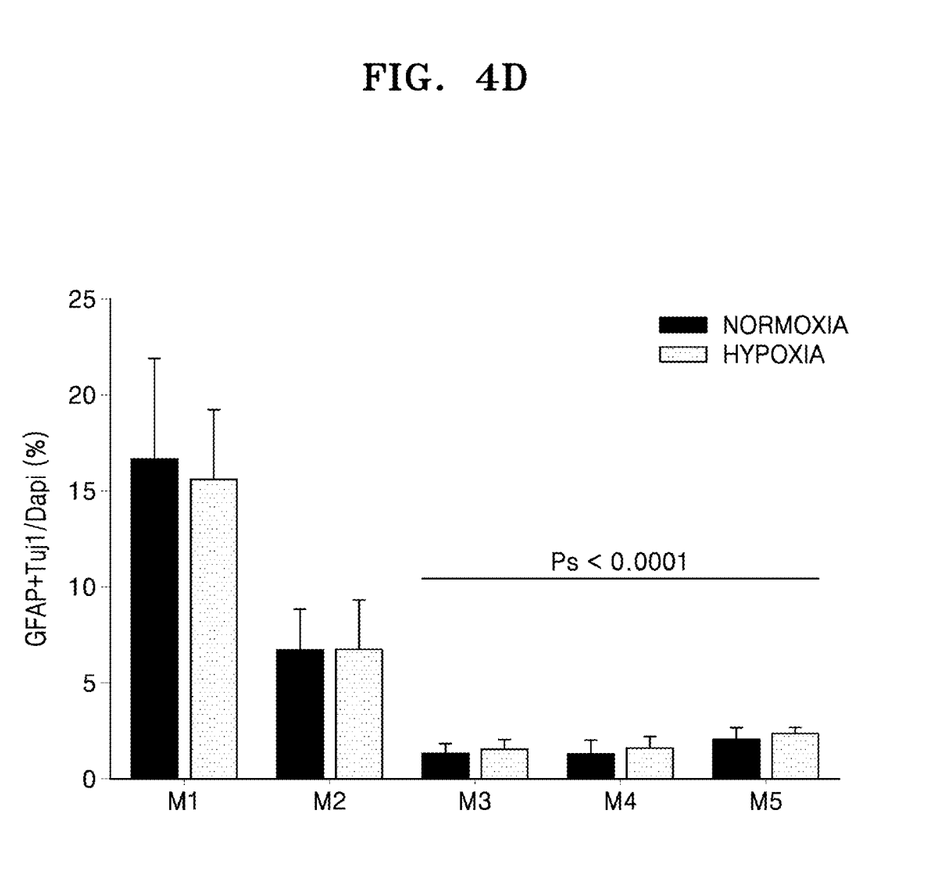

In FIG. 4D, in comparison with the fetal neural progenitor cells cultured under the general culture condition, the fetal neural progenitor cells cultured with DL-alpha-tocopherol acetate, alpha-tocopherol, or both DL-alpha-tocopherol acetate and alpha-tocopherol showed lower frequency of expression of both GFAP and Tuj1 together (Ps<0.0001). In addition, among the general culture conditions, addition of the B27 supplement (M2) lowered frequency of expression of both GFAP and Tuj1 together, as compared to a case without the B27 supplement (M1) (hypoxia condition: P<0.003, general normoxia condition: P<0.001).

Figure 4E:
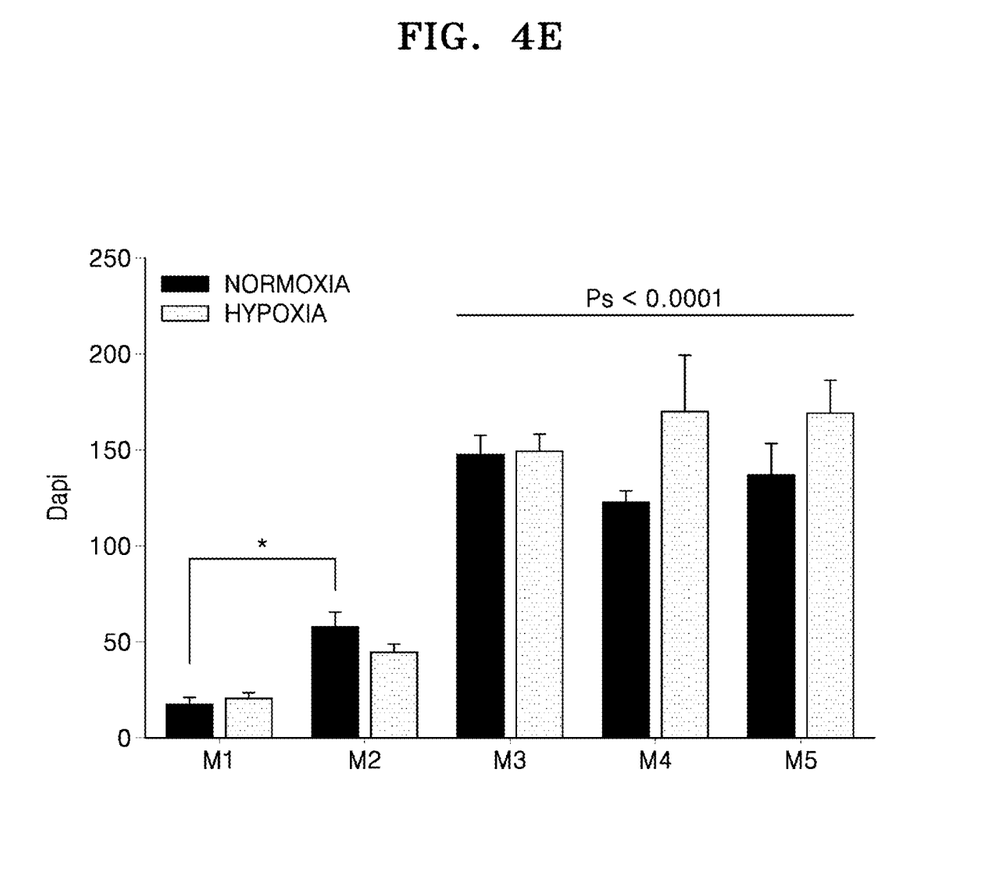

In FIG. 4E, in comparison with the fetal neural progenitor cells cultured under the general culture condition, the fetal neural progenitor cells cultured with DL-alpha-tocopherol acetate, alpha-tocopherol, or both DL-alpha-tocopherol acetate and alpha-tocopherol showed statistically significant increase in expression of Dapi (Ps<0.0001). In addition, among the general culture conditions, addition of the B27 supplement (M2) increased expression of Dapi, as compared to absence of B27 supplement (M1) (normoxia condition: Ps<0.008). In comparison with the fetal neural progenitor cells cultured with alpha-tocopherol under normoxia, the fetal neural progenitor cells cultured with alpha-tocopherol under hypoxia showed statistically significant increase in the expression of Dapi (M4: P<0.006).

Therefore, it was confirmed that addition of DL-alpha-tocopherol acetate, alpha-tocopherol, or both DL-alpha-tocopherol acetate and alpha-tocopherol lowered the positive cells for GFAP, a neuroglia cell marker, and for Tuj1, a neuron marker, and led to higher expression of Dapi, as compared with those found in the cases under the general culture condition.

The invention claimed is:
1. A method for proliferating a neural progenitor cell, the method comprising:
   culturing the neural progenitor cell in a medium comprising an antibiotic, a B27 supplement and a growth factor, and a mixture of tocopherol and tocopherol acetate at a concentration of about 0.1 μg/ml to about 5 μg/ml, which is in addition to tocopherol and tocopherol acetate in the B27 supplement,
   wherein the neural progenitor cell proliferates in an undifferentiated state.

2. The method of claim 1, wherein the culturing of the neural progenitor cell is performed under a hypoxia condition.

3. The method of claim 1, wherein the mixture of tocopherol an tocopherol acetate are mixed at a ratio in a range of about 1:5 to about 5:1.

4. The method of claim 1, wherein the growth factor is basic fibroblast growth factor (bFGF) and epidermal growth factor (EGF).

5. The method of claim 4, wherein the growth factor is fibroblast growth factor 4 (FGF4).

6. The method of claim 2, wherein the hypoxia condition comprises atmospheric oxygen at a concentration in a range of about 0.1% to about 10%.

7. The method of claim 1, wherein the neural progenitor cell is a neural progenitor cell isolated from human fetuses.

8. The method of claim 1, wherein the medium comprises the B27 supplement at a concentration of 2% of a total amount of the medium.

9. The method of claim 1, further comprising prior to the culturing:
adding tocopherol and tocopherol acetate in the medium so that an initial concentration of the mixture of tocopherol and tocopherol acetate in the medium is about 0.1 µg/ml to about 5 µg/ml; and
further adding an antibiotic, a B27 supplement and a growth factor to the medium.

10. The method of claim 9,
wherein the medium is a mixed medium of DMEM/F12 (1:1),
the growth factor is basic fibroblast growth factor (bFGF) and epidermal growth factor (EGF), and
the medium comprises the B27 supplement at a concentration of 2% of a total amount of the medium.

11. The method of claim 9, wherein the increased proliferation is measured by cell viability, and the cell viability increases at least ten times by adding the mixture of tocopherol and tocopherol acetate, separately from the B27 supplement, in the medium.

12. The method of claim 9, wherein the increased proliferation is measured by a cell count, and the cell count increases at least four times by adding the mixture of tocopherol and tocopherol acetate, separately from the B27 supplement, in the medium.

* * * * *